United States Patent
Ameri et al.

(10) Patent No.: US 9,254,380 B2
(45) Date of Patent: Feb. 9, 2016

(54) MRI COMPATIBLE TACHYCARDIA LEAD

(75) Inventors: Masoud Ameri, Maple Plain, MN (US); Yingbo Li, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 612 days.

(21) Appl. No.: 12/880,703

(22) Filed: Sep. 13, 2010

(65) Prior Publication Data
US 2011/0093054 A1    Apr. 21, 2011

Related U.S. Application Data

(60) Provisional application No. 61/252,915, filed on Oct. 19, 2009.

(51) Int. Cl.
*A61N 1/05*     (2006.01)
*A61N 1/375*    (2006.01)
*A61N 1/08*     (2006.01)

(52) U.S. Cl.
CPC .......... *A61N 1/0563* (2013.01); *A61N 1/05* (2013.01); *A61N 1/375* (2013.01); *A61N 2001/0585* (2013.01); *A61N 2001/086* (2013.01)

(58) Field of Classification Search
CPC ....... A61N 1/056; A61N 1/05; A61N 1/3752; A61N 1/0563; A61N 2001/086
USPC .................. 607/2, 9, 116, 119, 122
See application file for complete search history.

(56) References Cited

U.S. PATENT DOCUMENTS

| | | | |
|---|---|---|---|
| 3,614,692 A | 10/1971 | Rozelle et al. | |
| 4,131,759 A | 12/1978 | Felkel | |
| 4,135,518 A | 1/1979 | Dutcher | |
| 4,146,036 A | 3/1979 | Dutcher et al. | |
| 4,209,019 A | 6/1980 | Dutcher et al. | |
| 4,253,462 A | 3/1981 | Dutcher et al. | |
| 4,350,169 A | 9/1982 | Dutcher et al. | |
| 4,381,013 A | 4/1983 | Dutcher | |
| 4,404,125 A | 9/1983 | Abolins et al. | |

(Continued)

FOREIGN PATENT DOCUMENTS

CN    1762510 A    4/2006
CN    1905789 A    1/2007

(Continued)

OTHER PUBLICATIONS

International Search Report and Written Opinion issued in PCT/US2012/055673, mailed Dec. 13, 2012, 10 pages.
International Search Report and Written Opinion issued in PCT/US2009/038629, mailed Jun. 29, 2009, 11 pages.
Gray, Robert W. et al., "Simple design changes to wires to substantially reduce MRI-induced heating at 1.5 T: implications for implanted leads", Magnetic Resonance Imaging 23 (2005) 887-891.

(Continued)

*Primary Examiner* — Christopher D Koharski
*Assistant Examiner* — Pamela M Bays
(74) *Attorney, Agent, or Firm* — Faegre Baker Daniels LLP

(57) ABSTRACT

A medical device lead includes a proximal connector configured to couple the lead to a pulse generator, an insulative lead body extending distally from the proximal connector, and a conductor assembly extending distally from the proximal connector within the lead body. The conductor assembly includes a conductor having a proximal end electrically coupled to the connector and a distal end electrically coupled to a defibrillation coil. A first portion of the defibrillation coil is exposed at an outer surface of the medical device lead and a second portion of the defibrillation coil is insulated at the outer surface of the medical device lead.

6 Claims, 4 Drawing Sheets

(56) References Cited

U.S. PATENT DOCUMENTS

| | | | |
|---|---|---|---|
| 4,437,474 A | 3/1984 | Peers-Trevarton |
| 4,484,586 A | 11/1984 | McMickle et al. |
| 4,493,329 A | 1/1985 | Crawford et al. |
| 4,574,800 A | 3/1986 | Peers-Trevarton |
| 4,643,202 A | 2/1987 | Roche |
| 4,643,203 A | 2/1987 | Labbe |
| 4,649,938 A | 3/1987 | McArthur |
| 4,869,970 A | 9/1989 | Gulla et al. |
| 5,002,067 A | 3/1991 | Berthelsen et al. |
| 5,003,975 A | 4/1991 | Hafelfinger et al. |
| 5,020,545 A | 6/1991 | Soukup |
| 5,056,516 A | 10/1991 | Spehr |
| 5,074,313 A | 12/1991 | Dahl et al. |
| 5,144,960 A | 9/1992 | Mehra et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camp et al. |
| 5,243,911 A | 9/1993 | Dow et al. |
| 5,246,014 A | 9/1993 | Williams et al. |
| 5,259,395 A | 11/1993 | Li |
| 5,300,108 A | 4/1994 | Rebell et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,542,173 A | 8/1996 | Mar et al. |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,649,974 A * | 7/1997 | Nelson et al. ............. 607/122 |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,701,191 B2 | 3/2004 | Schell |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,920,361 B2 | 7/2005 | Williams |
| 6,925,334 B1 | 8/2005 | Salys |
| 6,944,489 B2 | 9/2005 | Zeijlemaker et al. |
| 6,949,929 B2 | 9/2005 | Gray et al. |
| 6,978,185 B2 | 12/2005 | Osypka |
| 6,985,755 B2 | 1/2006 | Cadieux et al. |
| 6,985,775 B2 | 1/2006 | Reinke et al. |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,242,987 B2 | 7/2007 | Holleman et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,610,101 B2 | 10/2009 | Wedan et al. |
| 7,630,761 B2 | 12/2009 | Salo et al. |
| 7,689,291 B2 | 3/2010 | Polkinghorne et al. |
| 7,765,005 B2 | 7/2010 | Stevenson |
| 7,853,332 B2 | 12/2010 | Olsen et al. |
| 7,877,150 B2 | 1/2011 | Hoegh et al. |
| 7,912,552 B2 | 3/2011 | Przybyszewski |
| 7,917,213 B2 | 3/2011 | Bulkes et al. |
| 7,933,662 B2 | 4/2011 | Marshall et al. |
| 7,953,499 B2 | 5/2011 | Knapp et al. |
| 7,986,999 B2 | 7/2011 | Wedan et al. |
| 7,991,484 B1 | 8/2011 | Sengupta et al. |
| 8,000,801 B2 | 8/2011 | Stevenson et al. |

(56) References Cited

U.S. PATENT DOCUMENTS

| | | |
|---|---|---|
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,306,630 B2 | 11/2012 | Stubbs et al. |
| 8,315,715 B2 | 11/2012 | Erickson |
| 8,391,994 B2 | 3/2013 | Foster et al. |
| 8,401,671 B2 | 3/2013 | Wedan et al. |
| 8,543,209 B2 | 9/2013 | Tyers et al. |
| 8,543,218 B2 | 9/2013 | Erickson |
| 8,666,508 B2 | 3/2014 | Foster et al. |
| 8,666,512 B2 | 3/2014 | Walker et al. |
| 8,670,840 B2 | 3/2014 | Wedan et al. |
| 8,676,351 B2 | 3/2014 | Foster et al. |
| 8,688,236 B2 | 4/2014 | Foster |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1* | 7/2003 | Villaseca et al. ............ 607/122 |
| 2003/0204217 A1 | 10/2003 | Greatbatch |
| 2004/0014355 A1* | 1/2004 | Osypka et al. ............... 439/502 |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1* | 5/2004 | Gardeski et al. ............. 606/129 |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1* | 9/2007 | Williams ............................ 607/2 |
| 2007/0255378 A1 | 11/2007 | Polkinghorne et al. |
| 2008/0009905 A1 | 1/2008 | Zeijlemaker |
| 2008/0033497 A1* | 2/2008 | Bulkes et al. ..................... 607/9 |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1* | 5/2008 | Geistert ........................ 607/116 |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0171421 A1* | 7/2009 | Atalar et al. ...................... 607/63 |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0103215 A1 | 4/2010 | Iriguchi |
| 2010/0106215 A1 | 4/2010 | Stubbs et al. |
| 2010/0114277 A1* | 5/2010 | Zhao ..................... A61N 1/056<br>607/116 |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |

(56) References Cited

U.S. PATENT DOCUMENTS

| | | |
|---|---|---|
| 2010/0249892 A1 | 9/2010 | Bulkes et al. |
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2013/0325093 A1 | 12/2013 | Foster |
| 2014/0067030 A1 | 3/2014 | Walker et al. |
| 2014/0114383 A1 | 4/2014 | Foster et al. |
| 2014/0155972 A1 | 6/2014 | Foster et al. |
| 2014/0324139 A1 | 10/2014 | Foster et al. |

FOREIGN PATENT DOCUMENTS

| | | |
|---|---|---|
| CN | 101039619 A | 9/2007 |
| EP | 0897997 B1 | 2/2003 |
| EP | 1594564 A1 | 11/2005 |
| EP | 1852810 B1 | 11/2007 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03063953 A2 | 8/2003 |
| WO | WO03089045 A2 | 10/2003 |
| WO | WO2004073791 A1 | 9/2004 |
| WO | WO03063946 A2 | 4/2005 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO2010078552 A1 | 7/2010 |

OTHER PUBLICATIONS

International Search Report and Written Opinion issued in PCT/US2008/085518 on Oct. 29, 2009, 15 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
International Search Report and Written Opinion issued in PCT/US2010/048638, mailed Nov. 12, 2010, 12 pages.
International Search Report and Written Opinion issued in PCT/US2009/032838, mailed May 4, 2009, 14 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
Partial International Search Report issued in PCT/US2013/013432, mailed Jul. 17, 2013, 6 pages.
Partial International Search Report issued in PCT/US2013/037432, mailed Jul. 17, 2013, 6 pages.
Third Party Submission Under 37 CFR 1.290 filed in U.S. Appl. No. 14/056,746 on May 20, 2014, 13 pages.
International Search Report and Written Opinion issued in PCT/US2013/065517, mailed Dec. 20, 2013, 11 pgs.
"High Voltage Engineering and Testing, 2nd Edition", edited by Hugh M. Ryan, Institution of Engineering and Technology, 2001, 15 pages.
Avalanche Breakdown, Wikipedia Article, captured Apr. 6, 2010, [http://en.wikipedia.org/wiki/Avalanche_breakdown].
Basso, Christophe, "SPICE Model Simulates Spark-Gap Arrestor", Electronics Design, Strategy, and News (EDN), Jul. 3, 1997, 4 pages.
Citel Inc., Data Sheet, BH Series 2 Electrode Miniature Gas Discharge Tube Surge Arrester—8mm, May 14, 2009, 2 pages.
File History for U.S. Appl. No. 11/015,807, filed Dec. 17, 2004 to Cooke, Daniel J. et al.
Hayes, David L., Chapter 4, "Generator and Lead Selection" from book entitled "Cardiac Pacing and Defibrillation a Clinical Approach", John Wiley & Sons, (c) 2000 Mayo Foundation, p. 129-157.
International Search Report and Written Opinion issued in PCT/US2009/056843, mailed Dec. 29, 2009, 13 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2011/052541, dated Mar. 9, 2012, 22 pages.
International Search Report and Written Opinion issued in PCT/US2013/037432, mailed Nov. 19, 2013, 17 pages.
International Search Report and Written Opinion issued in PCT/US2013/057732, mailed Dec. 13, 2013, 11 pages.
Partial International Search Report issued in PCT/US2011/052541, mailed Dec. 6, 2011, 4 pages.
Static Spark Gap Analysis, captured Dec. 24, 2002, [http://www.richieburnett.co.uk/static.html].

* cited by examiner

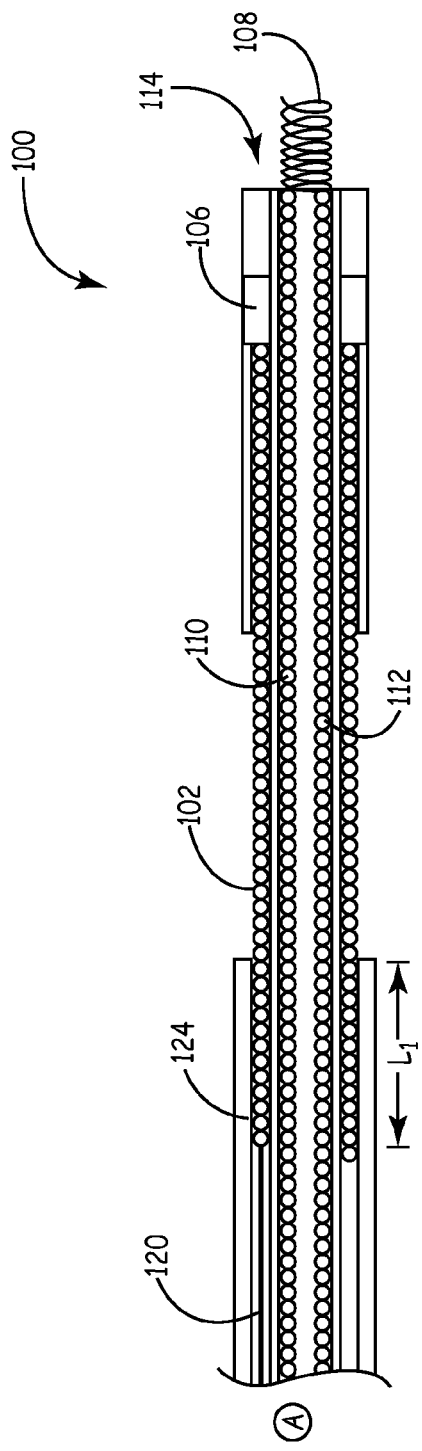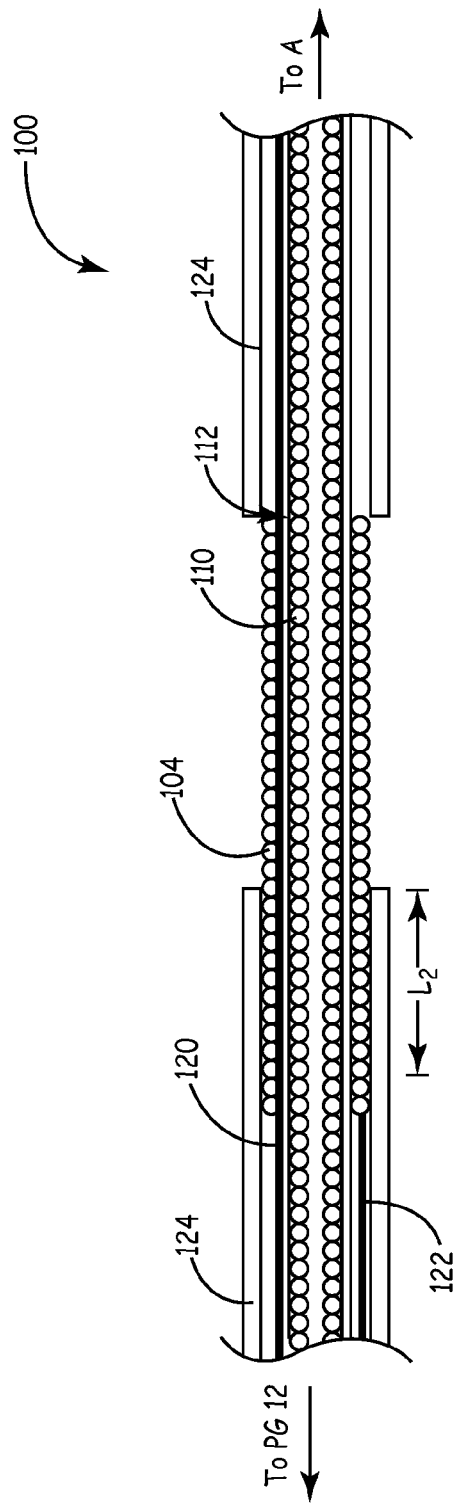

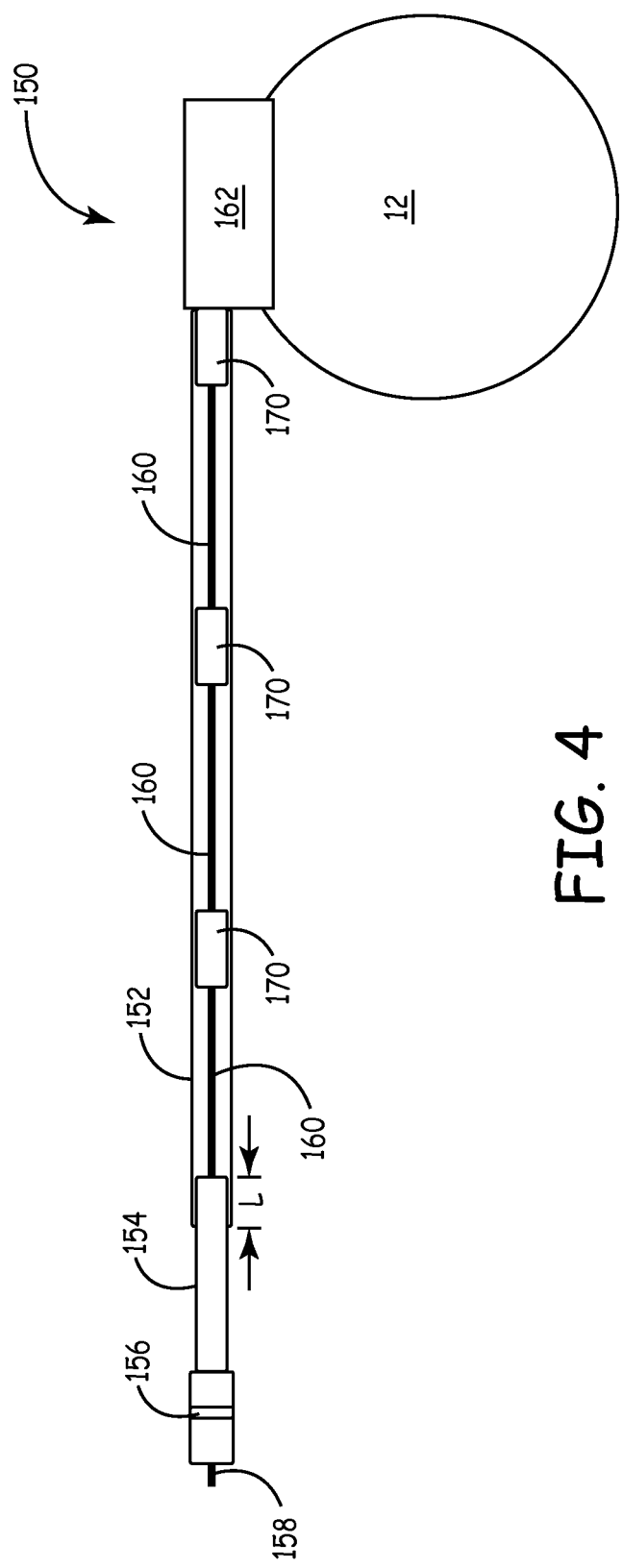

MRI COMPATIBLE TACHYCARDIA LEAD

CROSS-REFERENCE TO RELATED APPLICATION

This application claims priority to Provisional Application No. 61/252,915, filed Oct. 19, 2009, which is herein incorporated by reference in its entirety.

TECHNICAL FIELD

The present invention relates to implantable medical devices. More particularly, the present invention relates to MRI-compatible tachycardia lead constructions.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

The present invention relates to a medical device lead including a proximal connector configured to couple the lead to a pulse generator, an insulative lead body extending distally from the proximal connector, a conductor assembly extending distally from the proximal connector within the lead body. The conductor assembly includes a conductor having a proximal end electrically coupled to the connector and a distal end electrically coupled to a defibrillation coil. A first portion of the defibrillation coil is exposed at an outer surface of the medical device lead and a second portion of the defibrillation coil is insulated at the outer surface of the medical device lead.

In another aspect, a medical device lead includes a first connector configured to couple the lead to a pulse generator, an insulative lead body extending distally from the first connector, and a first conductor extending distally from the first connector within the lead body and having a proximal end electrically coupled to the first connector. A first defibrillation coil is exposed at an outer surface of the medical device lead, and a first high impedance coil is connected between the first conductor and the first defibrillation coil. The first high impedance coil is insulated at the outer surface of the medical device lead and has an impedance greater than the first conductor.

In a further aspect, a medical device lead includes one or more proximal connectors each configured to couple to a pulse generator, an insulative lead body extending distally from the one or more proximal connectors, and one or more conductors each extending distally from and electrically connected to one of the one or more proximal connectors. One or more defibrillation coils are each connected to a distal end of one of the one or more conductors. A first portion of each defibrillation coil is exposed at an outer surface of the medical device lead and a second portion of each defibrillation coil is insulated at the outer surface of the medical device lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3A is a cross-sectional view of a distal portion of a lead according to another embodiment of the present invention including two defibrillation coils that are each partially insulated.

FIG. 3B is a cross-sectional view of a portion of the lead proximal to the distal portion of the lead shown in FIG. 3A.

FIG. 4 is a schematic view of an implantable medical device including a lead having a plurality of high impedance coils in series with a conductive cable that extends through the lead body according to a further embodiment of the present invention.

Figure 1:
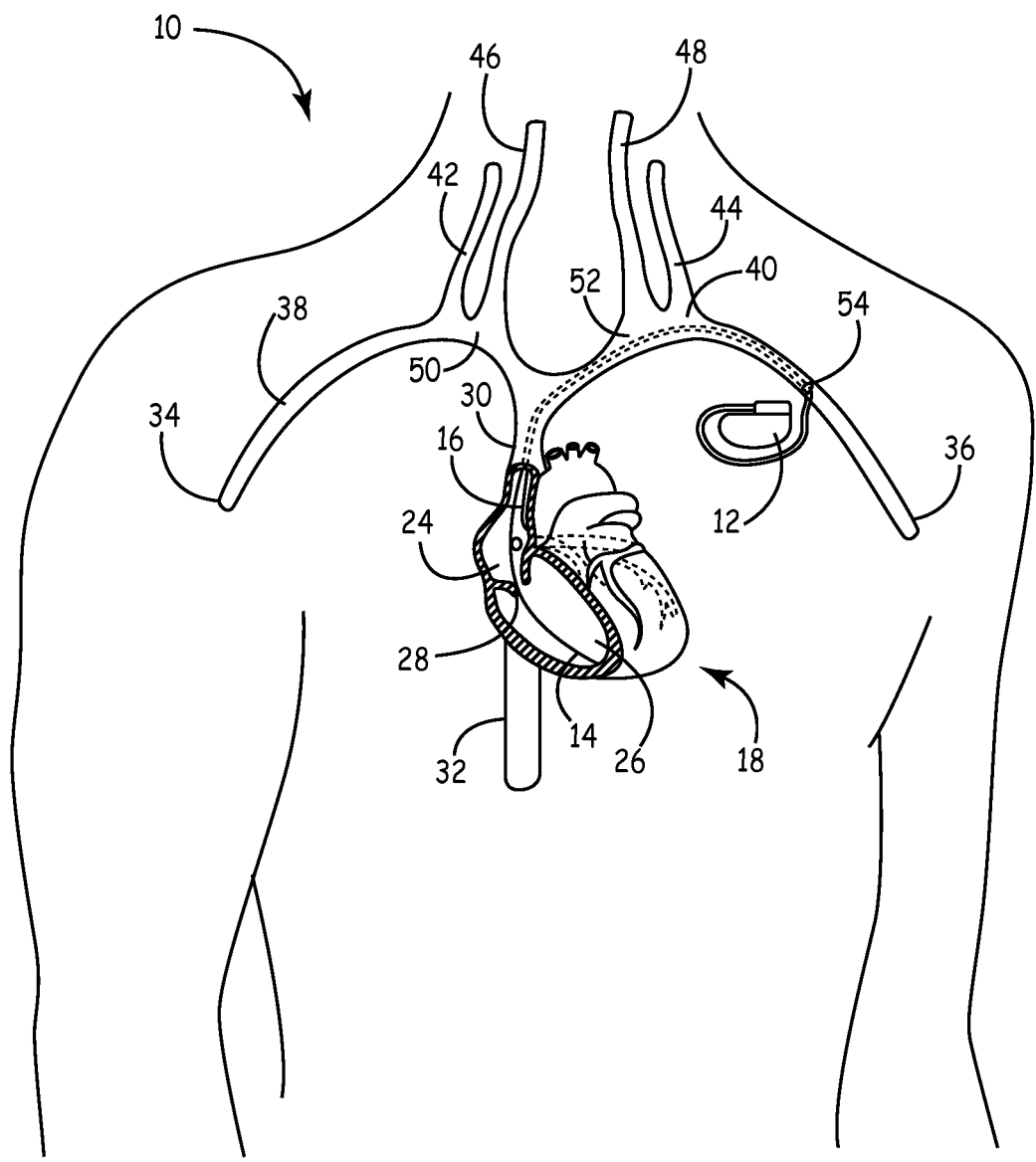
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired intracardiac implantation site, is generally coiled up in the subcutaneous pocket near the pulse generator 12.

Figure 2:
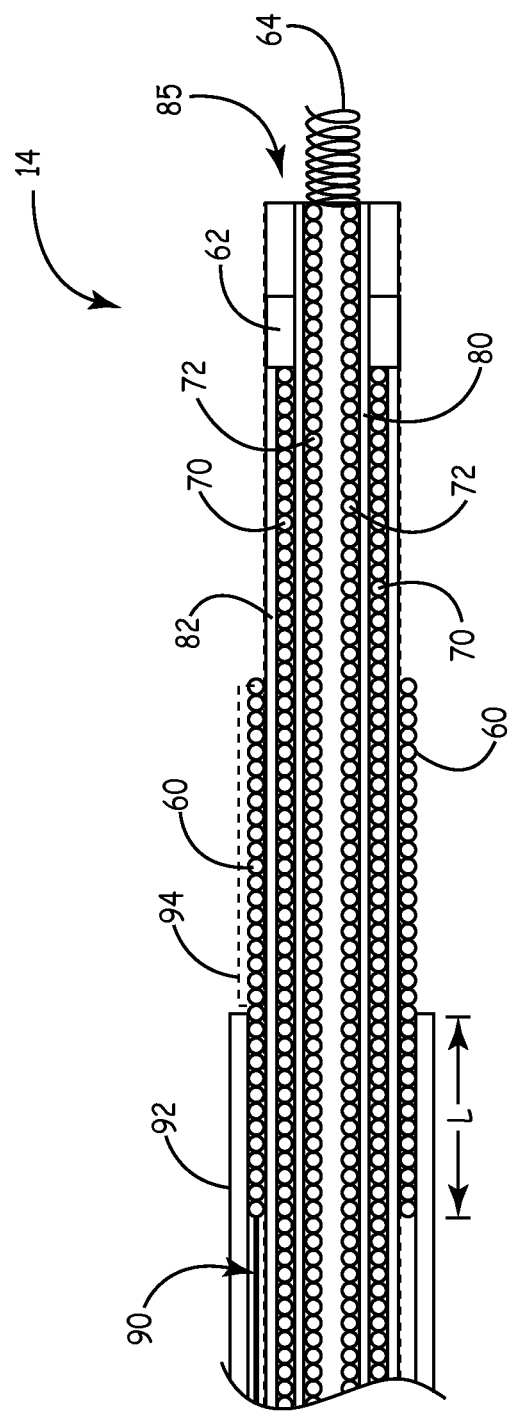
FIG. 2 is a cross-sectional view of a distal portion of a lead according to an embodiment of the present invention including a defibrillation coil that is partially insulated.

FIG. 2 is a cross-sectional view of the lead 14 according to an embodiment of the present invention. The lead 14 includes a defibrillation coil 60, and pacing or sensing electrodes 62 and 64. The defibrillation coil 60 may be used to deliver a high voltage therapy signal to a portion of the heart 18. The pacing or sensing electrodes 62 and 64 may be used for pacing, sensing, or both. In the embodiment shown, the electrode 62 is a ring electrode, and the electrode 64 includes a fixation helix. In some embodiments, the electrodes 62 and 64 include platinum or titanium coated with a combination of iridium oxide (IrOx), titanium/nickel (Ti/Ni), black platinum (Pt black), or tantalum oxide (TaO). The defibrillation coil 60 and the pacing or sensing electrodes 62 and 64 are located near a distal end portion of the lead 14. In alternative embodiments, the defibrillation and pacing or sensing electrodes are located elsewhere on the lead 14. The lead 14 may also alternatively include fewer or more electrodes.

The electrode 62 is coupled to a first conductive coil 70, and the electrode 64 is coupled to a second conductive coil 72. The second conductive coil 72 is surrounded by an insulative layer 80 to insulate the conductive coil 72 from other elements of the lead 14. In some embodiments, the insulative layer 80 extends from the proximal end to the distal end of the lead 14. An insulative layer 82 is also formed around the first conductor 70. In some embodiments, the insulative layer 82 extends from the proximal end of the lead 14 to the electrode 62. With this arrangement, the electrode 62 is exposed at the outer surface of the lead 14 to allow contact with adjacent tissue. The insulative layers 80 and 82 may be comprised of, for example, silicone material, Teflon, expanded polytetrafluoroethylene (ePTFE), polytetrafluoroethylene (PTFE), ethylene tetrafluoroethylene (ETFE), or another suitable non-conductive material. The electrodes 62 and 64, the conductive coils 70 and 72, and the insulative layers 80 and 82 combine to form the low voltage pacing/sensing portion 85 of the lead 14.

The first conductive coil 70 and the second conductive coil 72 extend through the lead 14 and are adapted for connection to the pulse generator 12 at the proximal end of the lead 14. In some embodiments, the first conductive coil 70 and the second conductive coil 72 are each coupled to a proximal connector at the proximal end of the lead 14. The connectors at the proximal end of the lead 14 are sized and shaped to interface with a connector block or other component of the pulse generator 12. The signals carried by the first conductive coil 70 and the second conductive coil 72 may be independently controlled by the pulse generator 12 such that different signals may be delivered to and/or received from the electrodes 62 and 64.

The defibrillation coil 60 is coupled to a conductive cable 90, which extends through the lead 14 and is adapted for connection to the pulse generator 12 at the proximal end of the lead 14. The conductive cable 90 may extend through the lead 14 in a lumen parallel to the conductive coils 70 and 72. The conductive cable 90 is surrounded by an insulating layer 92 at an exterior surface of the lead 14. In some embodiments, the conductive cable 90 is coupled to a proximal connector at the proximal end of the lead 14 that is sized and shaped to interface with a connector block or other component of the pulse generator 12. The conductive cable 90 delivers a high voltage defibrillation signal from the pulse generator 12 to the defibrillation coil 60. The lead 14 is arranged in the heart 18 such that the signal delivered by the defibrillation coil 60 depolarizes a critical mass of the heart muscle, terminates an arrhythmia, and allows normal sinus rhythm to be reestablished.

In a magnetic resonance imaging (MRI) environment, the radio frequency (RF) fields can induce a current in the conductive elements of the lead 14. This current may then be dissipated at the point of contact between the lead electrodes and adjacent tissue, resulting in elevated temperatures in the tissue. To reduce the RF current that is transmitted to the defibrillation coil 60 by the conductive cable 90, a length L of the defibrillation coil 60 is insulated at the exterior surface of the lead 14 by insulating layer 92. The insulated length L of the defibrillation coil 60 acts as an RF filter between the conductive cable 90 and the exposed portion of the defibrillation coil 60. More specifically, the inductance of a coil is directly proportional to the square of the radius of the coil. Thus, the inductance of the defibrillation coil 60 is large due to its large diameter. In some embodiments, the outside diameter of the defibrillation coil 60 is in the range of about 0.08 to 0.12 inch (about 2.0 to 3.0 mm). Consequently, the insulated length L of the defibrillation coil 60 reduces the amount of MRI-induced energy that is transmitted to the defibrillation coil 60 via the conductive cable 90. In some embodiments, the proximal and distal ends of the exposed portion of the defibrillation coil 60 are short circuited with an optional low impedance connection 94 (shown in phantom) to evenly distribute the high voltage signal across the exposed portion.

The inductance of a coil is also directly proportional to the square of the number of turns in the coil. Thus, in order to further reduce the amount of energy that is transmitted to the defibrillation coil 60, the turns of the defibrillation coil 60 may be tightly wound to maximize the inductance of the coil. Also, a unifilar coil may be used to minimize the space between adjacent turns and maximize the number of turns in the defibrillation coil 60. In some embodiments, filar of the defibrillation coil 60 has a diameter in the range of about 0.005 to 0.012 inch (about 0.125 mm to 0.305 mm).

In one exemplary implementation, the defibrillation coil 60 has a length of about 80 mm and an outside diameter of about 2.5 mm. The defibrillation coil 60 is a unifilar coil having a filar diameter of about 0.10 mm. The length L of the defibrillation coil 60 that is insulated is about 30 mm, and the distance separating the defibrillation coil 60 from the ring electrode 62 is about 12.5 mm. A lead 14 having this arrangement showed a reduction in heating of about 5-10° C. at the insulation-exposed coil interface of the defibrillation coil 60 compared to leads including a defibrillation coil 60 without a proximal insulated portion.

In alternative embodiments in which the defibrillation coil 60 is multifilar and/or in which the turns of the defibrillation coil 60 are not tightly wound, the length L of the defibrillation coil 60 that is insulated may be increased to increase the impedance of the insulated length L.

Thus, the length L, the number of turns, and the number of filars in the insulated section of the defibrillation coil 60 are selected to provide a reduction in MRI-induced energy in the exposed (i.e., non-insulated) section of the defibrillation coil 60 while minimizing the increase in resistance prior to the exposed portion of the defibrillation coil 60. In some embodiments, these parameters are selected to provide a total DC resistance in the conductive cable 90 and the insulated length L of less than about 5 Ω.

FIG. 3A is a cross-sectional view of a distal portion of a lead 100 according to another embodiment of the present invention. FIG. 3B is a cross-sectional view of a portion of the lead 100 proximal to the distal portion of the lead shown in FIG. 3A. The lead 100 is another exemplary configuration that may be employed as lead 14 in FIG. 1. As is shown, the proximal end of the distal portion of lead 100 shown in FIG. 3A is electrically coupled to the distal end of the proximal portion of lead 100 shown in FIG. 3B.

The lead 100 includes a distal defibrillation coil 102, a proximal defibrillation coil 104, a ring electrode 106, and a tip electrode 108. The distal defibrillation coil 102 and proximal defibrillation coil 104 may be used to deliver a high voltage therapy signal to different portions of the heart 18. The ring electrode 106 and/or the tip electrode 108 may be used for pacing, sensing, or both. In the embodiment shown, the ring electrode 106 is common with the distal defibrillation coil 102 and the tip electrode 108 includes a fixation helix. By making the ring electrode 106 common with the distal defibrillation coil 102, the diameter of the lead 100 is minimized. When shock therapy is not being delivered through the defibrillation coils 102 and 104, a pacing voltage may be generated between the electrodes 106 and 108. In alternative embodiments, the pacing or sensing electrodes are located elsewhere on the lead 100. The lead 100 may also alternatively include fewer or more electrodes.

The tip electrode 108 is coupled to a conductive coil 110, which is surrounded by an insulative layer 112 to insulate the conductive coil 110 from other elements of the lead 100. In some embodiments, the insulative layer 112 extends from the proximal end to the distal end of the lead 100. The insulative layer 112 may be comprised of, for example, silicone material, Teflon, expanded polytetrafluoroethylene (ePTFE), polytetrafluoroethylene (PTFE), ethylene tetrafluoroethylene (ETFE), or another suitable non-conductive material. The electrodes 106 and 108, the conductive coil 110, and the insulative layer 112 combine to form the low voltage pacing/sensing portion 114 of the lead 100.

The conductive coil 110 extends through the lead 100 and is adapted for connection to the pulse generator 12 at the proximal end of the lead 100. In some embodiments, the conductive coil 110 is coupled to a proximal connector at the proximal end of the lead 100. The connectors at the proximal end of the lead 100 are sized and shaped to interface with a connector block or other component of the pulse generator 12.

The distal defibrillation coil 102 is coupled to a conductive cable 120, and the proximal defibrillation coil 104 is coupled to a conductive cable 122. The conductive cables 120 and 122 extend through the lead 100 and are adapted for connection to the pulse generator 12 at the proximal end of the lead 100. In some embodiments, the conductive cables 120 and 122 may extend through the lead 100 in separate lumens parallel to the conductive coil 110. The conductive cable 120 is surrounded by an insulating layer 112 at an exterior surface of the lead 100. In some embodiments, the conductive cables 120 and 122 are each coupled to a proximal connector at the proximal end of the lead 100 that is sized and shaped to interface with a connector block or other component of the pulse generator 12. The conductive cables 120 and 122 delivers a high voltage defibrillation signal from the pulse generator 12 to the defibrillation coils 102 and 104, respectively.

To reduce the RF current that is transmitted to the defibrillation coils 102, 104 by the conductive cables 120 and 122, a length $L_1$ of the defibrillation coil 102 and a length $L_2$ of the defibrillation coil 104 are insulated at the exterior surface of the lead 100 by insulating layer 124. The insulated lengths $L_1$, $L_2$ act as RF filters between the conductive cables 120, 122 and the exposed portions of the defibrillation coils 102, 104, respectively. Consequently, the insulated lengths $L_1$, $L_2$ reduce the amount of MRI-induced energy that is transmitted to the defibrillation coils 102, 104, respectively. In addition, the portion of the defibrillation coil 102 that is insulated between the ring electrode 106 and the exposed portion of the defibrillation coil 102 may provide a further reduction in the amount of MRI-induced energy that is transmitted to the defibrillation coil 102 and/or the ring electrode 106.

The inductance of a coil is also directly proportional to the square of the number of turns in the coil. Thus, in order to further reduce the amount of energy that is transmitted to the defibrillation coils 102, 104, the turns of the defibrillation coils 102, 104 may be tightly wound to maximize the inductance of the coil. Also, unifilar coils may be used to minimize the space between adjacent turns and maximize the number of turns in the defibrillation coils 102, 104. In alternative embodiments in which the defibrillation coil is multifilar and/or in which the turns of the defibrillation coil are not tightly wound, the lengths $L_1$, $L_2$ of the defibrillation coils 102, 104 that are insulated may be increased to increase the impedance of the insulated lengths $L_1$, $L_2$.

Thus, the lengths $L_1$, $L_2$, the number of turns, and the number of filars in the insulated section of the defibrillation coils 102, 104 are selected to provide a reduction in MRI-induced energy in the exposed (i.e., non-insulated) sections of the defibrillation coils while minimizing the increase in resistance prior to the exposed portion of the defibrillation coils 102, 104. In some embodiments, these parameters are selected to provide a total DC resistance of the conductive cable 120 and the insulated length $L_1$ of less than about 5 Ω, and a total DC resistance of the conductive cable 122 and the insulated length $L_2$ of less than about 5 Ω.

In an alternative embodiment, the diameters of the exposed portions of the defibrillation coils 102, 104 may be increased to make the outer diameter of the defibrillation coils 102, 104 substantially equal to the outer diameter of the insulating layer 124. As a result, the lead 100 has a uniform outer diameter along its length. In one example implementation, a second, larger coil having an outer diameter substantially equal to the outer diameter of the insulating layer 124 is arranged around and in contact with the exposed portion of each of the defibrillation coils 102, 104. In another example implementation, the thickness of the insulating layer 112 is increased under the exposed portion of each of the defibrillation coils 102, 104 to increase the outer diameter of the defibrillation coils 102, 104 to be substantially equal to the outer diameter of the insulating layer 124.

FIG. 4 is a schematic view of an implantable medical device 150 including a pulse generator 12 and a lead 152 according to a further embodiment of the present invention. The lead 152 includes features that may be incorporated into either lead 14 or lead 100 described above. The lead 152 includes a defibrillation coil 154, a ring electrode 156 and a tip electrode 158. The defibrillation coil 154, the ring electrode 156, and the tip electrode 158 are located near a distal end portion of the lead 152. The lead 152 may also alternatively include fewer or more electrodes.

The defibrillation coil 154 is coupled to a conductive cable 160, which extends through the lead 150 and is adapted for connection to the pulse generator 12 at the proximal end of the lead 150. While not shown in FIG. 4, electrodes 156 and 158 are also electrically coupled to the pulse generator, such as via conductive coils as shown in FIGS. 2, 3A, and 3B, for example. In some embodiments, the conductive cable 160 is coupled to a proximal connector at the proximal end of the lead 14 that is sized and shaped to interface with a connector block 162 or other component of the pulse generator 12. The conductive cable 160 delivers a high voltage defibrillation signal from the pulse generator 12 to the defibrillation coil 154. The lead 152 is arranged in the heart 18 such that the signal delivered by the defibrillation coil 154 depolarizes a critical mass of the heart muscle, terminates an arrhythmia, and allows normal sinus rhythm to be reestablished.

As in the embodiments described above, a length L of the defibrillation coil 154 is insulated to increase the inductance between the conductive cable 160 and the exposed portion of the defibrillation coil 154. In the embodiment shown in FIG. 4, high impedance coils 170 are coupled in series with the conductive cable 160. The high impedance coils 170 provide an additional reduction in the amount of MRI-induced energy that is transmitted to the defibrillation coil 154. In addition, a high impedance coil 170 may be connected in series with the conductive cable 160 proximate the pulse generator 12 to reduce heating of the pulse generator housing. The high impedance coils 170 may be arranged periodically along the length of the conductive cable 160. In some embodiments, the length of the conductive cable 160 between adjacent high impedance coils 170 is less than one quarter wavelength ($\lambda/4$) of a signal carried by the conductive cable 160. This minimizes the energy picked up by the conductive cable 160 in an MRI environment.

In summary, embodiments of the present invention relate to a medical device lead including a proximal connector configured to couple the lead to a pulse generator, an insulative lead body extending distally from the proximal connector, a conductor assembly extending distally from the proximal connector within the lead body. The conductor assembly includes a conductor having a proximal end electrically coupled to the connector and a distal end electrically coupled to a defibrillation coil. A first portion of the defibrillation coil is exposed at an outer surface of the medical device lead and a second portion of the defibrillation coil is insulated at the outer surface of the medical device lead. The insulated portion of the defibrillation coil, which has a high impedance due to its relatively large diameter, acts as a filter for the radio frequency (RF) energy that is picked up by the conductor in a magnetic resonance imaging (MRI) environment. This reduces the transfer of RF energy to the defibrillation electrode, thereby decreasing the amount of heating of the tissue around the electrode.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
   a first connector configured to couple the lead to a pulse generator;
   an insulative lead body extending distally from the first connector;
   a first cable conductor extending distally from the first connector within the lead body and having a first segment having a proximal end coupled to the first connector, a second segment, and a third segment, the first cable conductor extending in a straight configuration within the lead body along each of the first, second, and third segments;
   a first defibrillation coil exposed at an outer surface of the medical device lead, the first defibrillation coil having a proximal end that is electrically connected to a distal end of the third segment of the first cable conductor; and
   a first high impedance coil connected in series to a second high impedance coil, a distal end of the first segment of the first cable conductor coupled to a proximal end of the first high impedance coil, a proximal end of the second segment of the first cable conductor coupled to a distal end of the first high impedance coil, a distal end of the second segment of the first cable conductor coupled to a proximal end of the second high impedance coil, and a distal end of the second high impedance coil coupled to a proximal end of the third segment of the first cable conductor, wherein each of the first segment of the first cable conductor, the first high impedance coil, the second segment of the first cable conductor, the second high impedance coil, the third segment of the first cable conductor, and the first defibrillation coil are respectively electrically connected to one another in series, wherein each of the first, second, and third segments of the first cable conductor has a respective length that is less than one quarter of a wavelength of a signal carried by the first cable conductor and each of the first high impedance coil and the second high impedance coil is insulated at the outer surface of the medical device lead and has an impedance greater than the first cable conductor.

2. The medical device lead of claim 1, wherein the first defibrillation coil is unifilar.

3. The medical device lead of claim 2, wherein opposing ends of the first defibrillation coil are short circuited.

4. The medical device lead of claim 3, wherein the insulative lead body comprises a layer of insulation that extends over a portion of the first defibrillation coil and terminates proximally of the outer surface to expose the first defibrillation coil distally of the layer of insulation.

5. The medical device lead of claim 4, wherein the first high impedance coil and the first cable conductor have a total DC resistance of less than about 5 Ω.

6. The medical device lead of claim 5, and further comprising:

a second connector configured to couple the lead to the pulse generator;

a second cable conductor having a proximal end electrically coupled to the second connector;

a second defibrillation coil exposed at an outer surface of the medical device lead; and a third high impedance coil connected between the second conductor and the second defibrillation coil, wherein the third high impedance coil is insulated at the outer surface of the medical device lead and has an impedance greater than the second conductor.

\* \* \* \* \*